US008852618B2

(12) United States Patent
Clough

(10) Patent No.: US 8,852,618 B2
(45) Date of Patent: Oct. 7, 2014

(54) INSECTICIDAL MIXTURE CONTAINING GAMMA-CYHALOTHRIN

(75) Inventor: Martin Stephen Clough, Bracknell (GB)

(73) Assignee: Syngenta Limited, Guildford (GB)

( * ) Notice: Subject to any disclaimer, the term of this patent is extended or adjusted under 35 U.S.C. 154(b) by 824 days.

(21) Appl. No.: 12/633,063

(22) Filed: Dec. 8, 2009

(65) Prior Publication Data

US 2010/0081714 A1  Apr. 1, 2010

Related U.S. Application Data

(62) Division of application No. 10/484,745, filed as application No. PCT/GB02/03181 on Jul. 10, 2002, now Pat. No. 7,906,127.

(30) Foreign Application Priority Data

Jul. 25, 2001 (GB) .................................. 0118137.9

(51) Int. Cl.
| | |
|---|---|
| A01N 25/02 | (2006.01) |
| A01N 53/14 | (2006.01) |
| A01N 53/00 | (2006.01) |
| A01N 25/00 | (2006.01) |

(52) U.S. Cl.
CPC .............. *A01N 53/00* (2013.01); *A01N 25/006* (2013.01); *A01N 25/02* (2013.01)
USPC ................... 424/405; 424/406; 28/28; 28/89; 28/144; 28/229.3; 28/594

(58) Field of Classification Search
None
See application file for complete search history.

(56) References Cited

U.S. PATENT DOCUMENTS

| | | | |
|---|---|---|---|
| 4,183,948 A | 1/1980 | Huff | |
| 4,362,722 A | 12/1982 | Stubbs | |
| 4,512,931 A | 4/1985 | Robson | |
| 4,857,510 A | 8/1989 | Knauf et al. | |
| 5,661,164 A | 8/1997 | Otsu et al. | |
| 6,159,991 A | 12/2000 | Saito | |
| 6,919,464 B1 | 7/2005 | Crouse et al. | |
| 7,030,095 B2 | 4/2006 | Janssen et al. | |
| 2002/0115565 A1 | 8/2002 | Asrar et al. | |
| 2003/0108585 A1 | 6/2003 | Roe et al. | |
| 2004/0235959 A1 | 11/2004 | Lahm et al. | |

FOREIGN PATENT DOCUMENTS

| | | | |
|---|---|---|---|
| CA | 2423995 | * | 4/2002 |
| CA | 2423995 A1 | | 4/2002 |
| CA | 2424018 | | 4/2002 |
| CA | 2424018 A1 | | 4/2002 |
| CA | 2424096 | | 4/2002 |
| CA | 2424096 A1 | | 4/2002 |
| CA | 2429218 | | 6/2002 |
| CA | 2429218 A1 | | 6/2002 |
| CH | 689326 A5 | | 4/1995 |
| EP | 0237227 A1 | | 9/1987 |
| EP | 0771526 A2 | | 5/1997 |
| EP | 0988788 A1 | | 3/2000 |
| FR | 2720230 A1 | | 12/1995 |
| JP | 63 126805 A2 | | 5/1988 |
| JP | 63126805 A2 | | 5/1988 |
| JP | 63126805 | | 5/1998 |
| WO | WO 86 07525 A1 | | 12/1986 |
| WO | WO 93 03618 A2 | | 3/1993 |
| WO | WO 95 22902 A1 | | 8/1995 |
| WO | WO 95 33380 A1 | | 12/1995 |
| WO | WO 96 16543 A2 | | 6/1996 |
| WO | WO 97 06687 A1 | | 2/1997 |
| WO | WO 97 40692 A1 | | 11/1997 |
| WO | WO 00 02453 A1 | | 1/2000 |

OTHER PUBLICATIONS

Canadian Office Action (Appln. No. 2,452,515 filed: Jul. 10, 2002) mailing date Oct. 1, 2010 (pp. 1-2).
Allen et al, Transgenic & Conventional Insect & Weed Control Systems; Proceedings of the Beltwide Cotton Conference, vol. 2, 1065-1068 (1999), USA.
Anonymous; Pesticide Mixtures for Control of Insect and Acarid Pests, 10, 258 (Research Disclosure 25812 (1985).
Benson, et al; Economics of a Tracer/Karate Z Conventional Cotton Program vs. BT Cotton; Proceedings of the Beltwide Cotton Conference, vol. 2, 1143-1145 (1999), USA.
Bently, et al; Fluorinated Analogues of Chrysanthemic Acid, Pestic. Sci. 11, 156-164 (1980), England.
Boykin et al; Economics of a Karate Z/Tracer Conventional Cotton Program vs. BT Cotton: Two Year Results; Proceedings of the Beltwide Cotton Conference, vol. 2, 1090-1093 (2000), USA.
Crop Care Australasia PTY Ltd; "Karate Insecticide With Zeon Technology" Pamphlet (1999), Australasia.
Davey, et al; Efficacy of Cyhalothrin & Lambdacyhalothrin Against *Boophilus microplus* (Acari: Ixodidae); J. Econ. Entomol., vol. 85(6); 2286-2290 (1992), USA.
DOW Agrosciences; "Rescue" Insecticide Label (Short Residual, Vapour Action Insecticide for the Knockdown of *Helicoverpa* spp. In Cotton) (1999), USA.
Dowelanco Australia Ltd.; Details of Issue of Permit: Chlorpyrifos-Methyl / Cotton / Native Budworm, Cotton Bollworm, PER292, KP2OW206/Version 2 (1997), Australia (including Attachment 1, pp. 1-5).
Elzen et al; Evaluation of Tolerance to Insecticides in Tobacco Budworm & Bollworm Populations; Proceedings of the Beltwide Cotton Conference, vol. 2, 1289-1291 (1997), USA.
Harrison, et al; Control of Lepidoptera Pests in Cotton With Intrepid Experimental Insecticide; Proceedings of the Beltwide Cotton Conference, vol. 2, 1091-1092 (1977), USA (Continued)

Primary Examiner — Neil Levy

(57) ABSTRACT

Mixtures containing gamma-cyhalothrin [(S)-α-cyano-3-phenoxybenzyl (Z)-(1R,3R)-3-(2-chloro-3,3,3-trifluoro-1-propenyl)-2,2-dimethylcyclopropanecarboxylate] and another compound having insecticidal, nematicidal, acaricidal, molluscicidal, fungicidal, plant growth regulating or herbicidal activity are provided. Compositions containing the mixture and insecticidal methods using such mixtures or compositions are also provided.

4 Claims, No Drawings

(56) References Cited

OTHER PUBLICATIONS

Johnson, et al; Comparison of New Insecticides for the Control of the Bollworm (*Heliocoverpa zea*) & Tobacco Budworm (*Heliothis virescens*) in Arkansas; Proceedings of the Beltwide Cotton Conference, vol. 2, 947-949 (1997), USA.

Johnson, et al; Evaluation of Nonsteroidal Ecdysone Agonists (Confirm & Intrepid) for Control of Heliothine Species in Cotton; AAES Special Report 198, 249-254 (2000), USA.

Johnson, et al; Management of the Heliothine Complex Using Traditional & New Insecticides; Proceedings of the Beltwide Cotton Conference, vol. 2, 1100-1102 (2000), USA.

Kerns et al; New Insecticides & Tank Mix Combinations for Worm Control in Lettuce; Univ. Arizona College of Agriculture Vegetable Report (1999) USA.

Kharboutli, et al; Outlook for Steward Insecticide for Control of Cotton Insects, 1998-1999; Arthropod Management Tests, vol. 25, 261-263 (2000), USA.

Lance et al; Evaluation of Insecticide Treatments for Control of Bollworm & Tobacco Budworm on Cotton; Arthropod Management Tests, vol. 25, 267-268 (1999), USA.

Micinski et al; Efficacy of selected insecticide mixtures for control of the bollworm/tobacco budworm complex. 1994; Arthropod Management Tests, Entomological Society of America, vol. 20, 207-208 (1995), USA (XP000617054).

Pan et al; Bibliographical Info. & Abstract, Ternary Complex Insecticide for Killing Mites & Insects, CN 1096632; Patent Application No. CN 93-107362 (1994).

Papa, et al; Efeito De Novo Inseticida (Avaunt 150), No Controle Da Lagarta Rosada, *Pectinophora gossypiella* (Lepidoptera:Gelechildae), vol. 20, 276-278 (1999), Brazil.

Pascual, et al; Brighton Crop Protection Conference—Pests & Diseases (3D8), 235-240 (1984), Spain.

Reed, et al; Evaluation of S1812 & Pyrethroid Combinations for Management of Heliothine Larvae on Cotton, 1999; Arthropod Management Tests, vol. 25, 276 (1999), USA.

Richardson, et al; XDE-225 (Gamma Cyhalothrin), A New Fully-Resolved Pyrethroid Product D First Year Yield Performance; Pacific Branch Entomology Society of America 85th Annual Meeting (2001), USA (One Page).

Robson et al; 1984 British Crop Protection Conference—Pests & Diseases, vol. 3, 853-857 (1984), England.

Sparks, et al; Pyrethroid-Synergist Mixtures: Toxicity, Resistance, & Field Efficacy Toward Pyrethroid Resistant Horn Flies (Diptera: Muscidae); Entomology Society of America, No. 0022-0493, 1567-1574 (1988), USA.

Sullivan, et al; Insecticidal Efficacy Against a Complex of Fall & Beet Armyworms & Soybean Looper in S.C. Cotton; Proceedings of the Beltwide Cotton Conference, vol. 2, 1034-1036 (1999), USA.

Sun et al; Bibliographical Info. & Abstract, Profenofos Resistance Risk in Cotton Bollworm, *Helicoverpa armigera* (Hubner) & The Synergistic Mixture; Nanjing Nongye Daxue Xuebao (2000).

Tank; Compatibility of IWD 4067 (500g/L Chlorpyrifos-Methyl EC) With Australian Cotton Insecticide Formulations; DowElanco Research Report, 1-12 (1997), Australia.

Valles et al; Temperature Effects on—Cyhalothrin Toxicity in Insecticide-Susceptible & Resistant German Cockroaches (Dictyoptera: Blattellidae); Florida Entomologist vol. 81(2), 193-201 (1988), USA.

Bentley et al., Fluorinated Analogues of Chrysanthemic Acid, Pestic. Sci., 1980, 11, p. 156-164.

Davey, R.B. et al., Efficacy of Cyhalothrin and Lambdacyhalothrin Against *Boopphilus microplus* (Acari: Ixodidae), Journal of Veterinary Entomology, 1992, 85(6), p. 2286-2290.

Slosser J.E. et al., "Cotton aphid response to irrigation and crop chemicals", Southwestern Entomologist, Mar. 2001, 26(1), p. 1-14.

Excerpt From Compendium of Pesticides Common Names; [online]; Retrieved on Jan. 24, 2012.

Tomlin, CDS., Excerpt From "The Pestocode Manual, Twelfth Edition", British Crop Protection Council, Copyright 2000.

Excerpt From AG Chem New Compound Review, vol. 20, 2002.

Excerpt From AG Chem New Compound Review, vol. 19, 2001.

Bentley et al., Table titled "Isomers", Pestic., Sc., 1980, 11, 156-64.

Canadian Office Action/Request for Re-Examination to Section 48.1 of the Patent Act for CA Patent Application No. 2452515, dated Sep. 3, 2013.

Schedule D Highlights of Prior Art being filed in support of Request for Re-Examination related to Canadian Office Action dated Sep. 3, 2013.

EP Decision of the Examining Division for EP Application No. 02 743 440.6 dated Jun. 12, 2009.

\* cited by examiner

INSECTICIDAL MIXTURE CONTAINING GAMMA-CYHALOTHRIN

CROSS-REFERENCE TO RELATED APPLICATIONS

This application is a divisional of U.S. Ser. No. 10/484,745, filed Oct. 22, 2004, which is a national stage of International Application No. PCT/GB2002/03181, filed Jul. 10, 2002, which claims priority to United Kingdom Application No. 0118137.9, filed Jul. 25, 2001, each of which are hereby incorporated by reference in their entirety.

BACKGROUND OF THE INVENTION

Field of the Invention

This invention relates to mixtures with insecticidal properties comprising two or more active ingredients, to compositions containing them and to methods of controlling unwanted pests using such mixtures or compositions. More particularly, the invention relates to mixtures containing gamma-cyhalothrin [(S)-α-cyano-3-phenoxybenzyl (Z)-(1R,3R)-3-(2-chloro-3,3,3-trifluoro-1-propenyl)-2,2-dimethylcyclopropanecarboxylate] and another compound having insecticidal, nematicidal, acaricidal, molluscicidal, fungicidal, plant growth regulating or herbicidal activity, to compositions containing the mixture and to insecticidal methods using such mixtures or compositions.

DETAILED DESCRIPTION OF THE INVENTION

Compounds having insecticidal, nematicidal, acaricidal, molluscicidal, fungicidal, plant growth regulating or herbicidal activity are hereinafter referred to as active ingredients.

(S)-α-Cyano-3-phenoxybenzyl (Z)-(1R,3R)-3-(2-chloro-3,3,3-trifluoro-1-propenyl)-2,2-dimethylcyclopropanecarboxylate and its insecticidal activity was disclosed by Bentley et al, Pestic. Sci. (1980), 11(2), 156-64.

Combining gamma-cyhalothrin and one or more further active ingredients can provide useful biological effects such as synergy against important pests such as *Heliothis virescens, Spodoptera littoralis* and *Myzus persicae.*

There is therefore provided a mixture of gamma-cyhalothrin and one or more further active ingredients.

It is preferred that the further active ingredient, other than gamma-cyhalothrin is an active ingredient having insecticidal, nematicidal or acaricidal activity.

Examples of suitable insecticides that may be used as a further active ingredient in the mixture of the invention may be any compound selected from:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate or any of their insecticidally active isomers;

b) Organophosphates, such as, methidathion, chlorpyrifos-methyl, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, chlorpyrifos-methyl, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as fenoxycarb, alanycarb, pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as lufenuron, novaluron, noviflumuron, teflubenzuron, diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tolfenpyrad, pyridaben, tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as diofenolan, clothianidin, thiacloprid, imidacloprid, thiacloprid, acetamiprid, nitenpyram or thiamethoxam;

m) Diacylhydrazines, such as halofenozide, tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Diafenthiuron;

s) Toxins of microbial origin such as *Bacillus thuringiensis* endo- or exotoxins;

t) Phenylpyrazoles such as fipronil, vanilliprole, etiprole or acetoprole; or u) Pyridalyl.

In addition to the major chemical classes of pesticide listed above, other pesticides having particular targets may be employed in the mixture if appropriate for the intended utility of the mixture. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the mixtures (for example acaricidal ovolarvicides, such as clofentezine, flubenzimine, hexythiazox or tetradifon; acaricidal motilicides, such as dicofol or propargite; acaricides, such as acequinocyl, fenazaquin, spirodiclofen, etoxazole, bromopropylate or chlorobenzilate; or growth regulators, such as hydramethylnon, cyromazine, methoprene, chlorfluazuron or diflubenzuron).

Examples of suitable insecticide synergists insecticides that may be used as a further active ingredient in the mixture of the invention include piperonyl butoxide, sesamex, safroxan and dodecyl imidazole.

The further active ingredient is preferably one or more of thiamethoxam, abamectin, emamectin benzoate, spinosad, chlorpyrifos, chlorpyrifos-methyl, profenofos, lufenuron, indoxacarb, lambda-cyhalothrin, pymetrozine, pirimicarb, methidathion, imidacloprid, acetamiprid, thiacloprid, fipronil, methoxyfenozide, chlorfenapyr, pyridaben, novaluron, pyridalyl, propargite and piperonyl butoxide.

The further active ingredient is more preferably one or more of thiacloprid, fipronil, methoxyfenozide, spinosad, profenofos, chlorfenapyr, pyridaben, emamectin benzoate and indoxacarb; or it is one or more of thiamethoxam, abamectin, emamectin benzoate, spinosad, chlorpyrifos, profenofos, lufenuron, indoxacarb and lambda-cyhalothrin.

Examples of suitable fungicides that may be used as a further active ingredient in the mixture of the invention may be any compound selected from:

(E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

Examples of suitable herbicides that may be used as a further active ingredient in the mixture of the invention may be any compound selected from:

A. 1,2,4-triazin-5-ones such as metamitron and metribuzin
B. dimethylpyrazoles such as benzofenap, pyrazolynate (pyrazolate) and pyrazoxyfen.
C. acylanilides such as propanil
D. amide herbicides such as benfluamid, bromobutide, carbetamide, flufenacet, isoxaben, naproanilide, napropamide, naptalam, propyzamide and tebutam
E. amino acids and salts and esters thereof, such as bialaphos and salts and esters thereof, glufosinate salts and esters thereof, glyphosate and salts and esters thereof, and sulfosate.
F. aryloxypropionates, including the optically active isomers thereof, such as clodinafop-propargyl, cyhalofop-butyl, diclofop & esters thereof eg methyl ester, fenoxaprop & esters thereof eg ethyl ester, fluazifop-butyl, haloxyfop and esters thereof, propaquizafop, quizalofop and esters thereof and quizalofop-p-tefuryl
G. arylanilides such as diflufenican, flamprop, flamprop-M and esters thereof
H. arylureas such as chlorbromuron, chlorotoluron, daimuron (dymron), dimefuron, diuron, fenuron, fluometuron, isoproturon, isouron, linuron, methabenzthiazuron, methyldymron, metobromuron, metoxuron, monolinuron, neburon and tebuthiuron
I. benzo-2,1,3-thiadiazin-4-one-dioxides such as bentazone
J. benzoic acids such as 2,3,6-trichlorobenzoic acid, chloramben and dicamba
K. bipyridyliums such as diquat and salts thereof, and paraquat and salts thereof
L. carbamates such as chlorpropham and propham, and phenylcarbamoyloxyphenyl carbamates such as desmedipham and phenmedipham
M. acetamides such as acetochlor, alachlor, butachlor, dimethachlor, dimethenamid and isomers thereof, metazachlor, metolachlor and isomers thereof, pretilachlor, propachlor, propisochlor and thenylchlor.
N. cyclohexanediones such as alloxydim and salts thereof, butroxydim, clethodim, cycloxydim, sethoxydim, tepraloxydim and tralkoxydim.
O. dihalobenzonitriles such as dichlobenil
P. dinitrophenols such as dinoterb and dinitro ortho-cresol (DNOC)
Q. diphenyl ethers such as acifluorofen and salts and esters thereof, aclonifen, bifenox, chlomethoxyfen, chlornitrofen, fluoroglycofen or salts or ester thereof, fomesafen, lactofen and oxyfluorfen.
R. dinitroanilines such as dinitramine, ethalfluralin, fluchloralin, oryzalin, pendimethalin, prodiamine and trifluralin.
S. haloalkanoic herbicides such as dalapon and trichloroacetic acid and salts thereof
T. hydroxybenzonitrile (HBN) herbicides such as bromoxynil and ioxynil, and HBN precursors such as bromofenoxim
U. hormone herbicides such as 2,4,5-trichlorophenoxyacetic acid, 2,4-dichlorophenoxyacetic acid, 2,4-dichlorophenoxybutyric acid, clopyralid, dichlorprop & dichlorprop-p, fluoroxypyr, 4-chloro-2-methoxyacetic acid (MCPA), MCPA-thioethyl, 4-(4-chloro-2-methylphenoxy)butyric acid (MCPB), mecoprop & mecoprop-p, picloram, thiazopyr and triclopyr.

V. imidazolinones such as imazapic, imazamox, imazamethabenz-methyl, imazapyr & isopropylammonium salts thereof, imazaquin and imazethapyr.

W. methyl isothiocyanate precursors such as dazomet.

X. miscellaneous herbicides such as ammonium sulfamate, asulam, azafenidin, benazolin, benzobicyclon/benbiclon, cinmethylin, clomazone, difenzoquat & salts thereof eg methyl sulphate salt, diflufenzopyr-sodium (SAN-835H), dimethipin, dimexyflam, diphenamid, dithiopyr, epoprodan, ethofumesate, etobenzanid, fluazolate, fentrazamide, flucarbazone, flumiclorac-pentyl, flumioxazin, flupoxam, flurenol-butyl, fluorochloridone, flurtamone, fluthiacet-methyl, hexazinone, mefenacet, oxadiazon, oxaziclomefone, pentoxazone, pyraflufen-ethyl, pyridatol/pyridafol, pyridate, isoxachlortole, isoxaflutole and sodium chlorate.

Y. organoarsenical herbicides such as disodium methylarsonate (DSMA) and monosodium methylarsonate (MSMA)

Z. organophosphorus herbicides such as anilofos and fosamine-sodium

AA. phosphorothioates such as butamifos, bensulide and piperophos

BB. pyridazinones such as chloridazon and norflurazon

CC. pyridones such as fluridone

DD. pyrimidinyloxybenzoic acids and salts and esters thereof, such as pyrithiobac-sodium, bispyribac-sodium, pyriminobac-methyl and pyribenzoxim.

EE. quinolinecarboxylic acids such as quimerac and quinclorac

FF. herbicide antidotes such as benoxacor, cloquintocet-mexyl, dichlormid, fenchlorazole-ethyl, fenclorim, fluxofenim, furilazole, naphthalic anhydride, oxabentrinil, mefenpyr-diethyl, N-(dichloroacetyl)-1-oxa-4-azaspirobicyclo-(4,5)-decane (AD-67), 3-dichloroacetyl-2, 2,5-trimethyloxazolidine (R-29148) and 2-dichloromethyl-2-methyl-1,3-dioxolane (MG-191).

GG. sulfamoylureas such as cyclosulfamuron.

HH. sulfonanilides such as chloransulam-methyl, diclosulam, florasulam, flumetsulam and metosulam.

II. sulfonylureas such as amidosulfuron, azimsulfuron, bensulfuron and esters thereof, chlorimuron & esters eg ethyl ester thereof, chlorsulfuron, cinosulfuron, ethametsulfuron-methyl, flazasulfuron, flupyrsulfuron and salts thereof, halosulfuron-methyl, ethoxysulfuron, imazosulfuron, iodosulfuron, metsulfuron and esters thereof, nicosulfuron, oxasulfuron, primisulfuron & esters eg methyl ester thereof, prosulfuron, pyrazosulfuron-ethyl, rimsulfuron, sulfometuron-methyl, sulfosulfuron, thifensulfuron-methyl, triasulfuron, tribenuron, tribenuron-methyl and triflusulfuron-methyl JJ. thiocarbamates such as butylate, cycloate, dimepiperate, S-ethyl dipropylthiocarbamate (EPTC), esprocarb, molinate, orbencarb, pebulate, prosulfocarb, thiobencarb, tiocarbazil, tri-allate and vernolate.

KK. triazine herbicides such as ametryn, atrazine, cyanazine, dimethametryn, prometon, prometryn, propazine, simazine, simetryn, terbuthylazine, terbutryn and trietazine.

LL. triazole herbicides such as amitrole.

MM. triazolinones such as carfentrazone-ethyl and sulfentrazone.

NN. triketones such as sulcotrione and mesotrione.

OO. uracils such as bromacil, lenacil and terbacil.

Examples of suitable plant growth regulators that may be used as a further active ingredient in the mixture of the invention may be any compound selected from ancymidol, chlormequat chloride, ethephon, flumetralin, flurprimidol, gibberellic acid, gibberellin A4/gibberellin A7, maleic hydrazide, mepiquat chloride, paclobutrazol, prohexadione calcium, thiadiazuron, trinexapac ethyl and uniconazole.

In order to apply the active ingredients to a pest, a locus of pest, or to a plant susceptible to attack by a pest, or, as a fungicide to a plant, to a seed of a plant, to the locus of the plant or seed, to soil or to any other growth medium, the active ingredients are usually formulated into a composition which includes, in addition to the active ingredients, a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting).

In one particular aspect the present invention therefore also provides novel insecticidal compositions comprising gamma cyhalothrin and one or more compounds possessing insecticidal, nematicidal, acaricidal, molluscicidal, fungicidal, plant growth regulating or herbicidal activity, an insecticidally inert carrier or diluent and, optionally, one or more surface active agents.

It is preferred that the ratio of gamma-cyhalothrin: other active ingredients is in the range 1:100 to 100:1 (for example 1:10 to 10:1) weight/weight.

It is preferred that the composition contains at least one compound other than gamma-cyhalothrin having activity against insects, acarines, or nematodes.

It is preferred that all compositions (both solid and liquid formulations) comprise, by weight, 0.0001 to 95%, more preferably 1 to 85%, for example 5 to 60%, of active ingredients. The composition is generally used for the control of pests or fungi such that the active ingredients are applied at a rate of from 0.1 g to 10 kg per hectare, preferably from 1 g to 6 kg per hectare, more preferably from 1 g to 1 kg per hectare.

When used in a seed dressing, the active ingredients are used at a rate of 0.0001 g to 10 g (for example 0.001 g or 0.05 g), preferably 0.005 g to 10 g, more preferably 0.005 g to 4 g, per kilogram of seed.

The formulated compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of active ingredients.

Dustable powders (DP) may be prepared by mixing the active ingredients with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing the active ingredients with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the active ingredients with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredients and one or more powdered solid diluents or carriers, or from pre-formed blank granules by absorbing the active ingredients (or a solution thereof, in a suitable agent) in a porous granular material (such as pumice, attapulgite clays, fuller's earth, kieselguhr, diatomaceous earths or ground corn cobs) or by adsorbing the active ingredients (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the active ingredients in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving the active ingredients in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining the active ingredients either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. The active ingredients are present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of the active ingredients. SCs may be prepared by ball or bead milling the active ingredients in a suitable medium, optionally with one or more dispersing agents, to produce a fine particle suspension of the compound. One or more wetting agents may be included in the composition and a suspending agent may be included to reduce the rate at which the particles settle. Alternatively, the active ingredients may be dry milled and added to water, containing agents hereinbefore described, to produce the desired end product.

Aerosol formulations comprise the active ingredients and a suitable propellant (for example n-butane). The active ingredients may also be dissolved or dispersed in a suitable medium (for example water or a water miscible liquid, such as n-propanol) to provide compositions for use in non-pressurised, hand-actuated spray pumps.

The active ingredients may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredients and, optionally, a carrier or diluent therefor. The polymeric shell may be produced by either an interfacial polycondensation reaction or by a coacervation procedure. The compositions may provide for controlled release of the active ingredients and they may be used for seed treatment. The active ingredients may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of the active ingredients). Such additives include surface active agents, spray additives based on oils, for example certain mineral oils or natural plant oils (such as soy bean and rape seed oil), and blends of these with other bio-enhancing adjuvants (ingredients which may aid or modify the action of the active ingredients.

The active ingredients may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The active ingredients may be applied by any of the known means of applying pesticidal or fungicidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

The active ingredients may also be incorporated into bait stations used to attract and control pests.

The active ingredients may also be incorporated into materials used in the construction or agricultural industries. They may, for example, be incorporated into plastics films or sheets used in the construction of buildings to protect them from pests such as termites.

The active ingredients may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of the active ingredients (for example 0.0001 to 10%, by weight) depending upon the purpose for which they are to be used.

The active ingredients may be used in mixtures with fertilisers (for example nitrogen-, potassium- or phosphorus-containing fertilisers). Suitable formulation types include granules of fertiliser. The mixtures suitably contain up to 25% by weight of the active ingredients. The invention therefore also provides a fertiliser composition comprising a fertiliser and the active ingredients.

The amount of composition of the present invention generally applied for the control of insect pests gives a rate of active ingredient from 0.01 to 10 kg per hectare, preferably from 0.1 to 6 kg per hectare.

The mixture of the invention is preferably presented in a single composition. However the components may be presented in separate containers, one containing gamma-cyhalothrin optionally in combination with a solid or liquid diluent, and the second containing a further active ingredient optionally in combination with a solid or liquid diluent. Alternatively the components may be presented in a two pack-container, one compartment of which contains gamma-cyhalothrin optionally in combination with a solid or liquid diluent and a second compartment which contains a further active ingredient optionally in combination with a solid or liquid diluent.

The contents of the two containers or the two compartments can then be admixed, for example by mixing both in water prior to administration.

In another aspect the present invention provides a method of combating insect, acarine or nematode include insect pests such as Lepidoptera, Diptera, Homoptera and Coleoptera (including *Diabrotica*, that is, corn rootworm), pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species include: *Myzus persicae* (aphid), *Aphis gossypii* (aphid), *Aphis fabae* (aphid), *Aedes aegypti* (mosquito), *Anopheles* spp. (mosquitos), *Culex* spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), *Aonidiella* spp. (scale insects), *Trialeurodes* spp. (white flies), *Bemisia tabaci* (white fly), *Blattella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), *Diabrotica* spp. (rootworms), *Agrotis* spp. (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus ni*, *Tetranychus cinnabarinus* (carmine spider mite), *Phyllcoptruta oleivora* (citrus rust mite), *Polyphagotarsonemus latus* (broad mite) and *Brevipalpus* spp. (mites).

Examples of pest species which may be controlled by the compositions of the invention include: *Myzus persicae* (aphid), *Aphis gossypii* (aphid), *Aphis fabae* (aphid), *Lygus* spp. (capsids), *Dysdercus* spp. (capsids), *Nilaparvata lugens*

(planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera* littoralis (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a mixture containing gamma-cyhalothrin and one or more compounds possessing insecticidal, nematicidal, acaricidal, molluscicidal, fungicidal, plant growth regulating or herbicidal activity to a pest, a locus of pest, or to a plant susceptible to attack by a pest, to a seed of a plant, to the locus of the plant or seed, to soil or to any other growth medium (for example a nutrient solution).

The term "plant" as used herein includes seedlings, bushes and trees. Furthermore, the fungicidal method of the invention includes protectant, curative, systemic, eradicant and antisporulant treatments.

The invention is illustrated by the following Examples.

Example 1

Test compositions were made up from technical active ingredient in 0.05% Synperonic NP8 with the exception of spinosad, for which Tracer 480SC diluted in water was used. For *Heliothis* and *Spodoptera* testing cotton leaves were sprayed in a Berkhard Potter Tower, left to dry for 1 hour and then placed on the top of pots containing twenty 1st instar *Heliothis virescens/Spodoptera littoralis* larvae. These were stored in a test holding room at 25° C. for 3 days and the test species assessed for mortality. For aphid testing Leaf discs were cut from excised Chinese cabbage leaves and placed on agar in test pots. R2 *Myzus persicae* were transferred from the culture on radish cotyledons and left overnight. The dried cotyledons were removed, leaving approximately 20-25 aphids on each leaf disc. The pots were sprayed in a Berkhard Potter Tower. Once dry, ventilated lids were placed on the top. These were stored in a Weiss Room at 20° C. for 3 days and the test species assessed for mortality. All tests included a Synperonic NP8 control. The results of the mortality assessments were adjusted for any mortality seen in the control test and analysed using the Colby equation to compare the mortality achieved with the mixture at each ratio to that expected from the individual ai's applied alone at the same rate. Any increase in the expected amount of mortality may be attributed to synergism. This is calculated in the following way: Expected mortality from mixture=% mortality of mixture partner A+(100%−% mortality of A)*(% mortality of mixture partner B). The results are set out in Tables I-III.

TABLE I

Results for test using *Heliothis virescens*

| Mixture partner | Ratio (gamma:ai's) | Rates applied (ppm) | | Observed % mortality | | | Expected % mortality with mixture | Observed-expected |
|---|---|---|---|---|---|---|---|---|
| | | Gamma | Other ai | Gamma | Other ai | Mixture | mixture | |
| Abamectin | 1:1 | 0.25 | 0.25 | 28 | 0 | 36 | 28 | 8 |
| | 1:1 | 0.50 | 0.50 | 28 | 0 | 25 | 28 | −3 |
| | 1:1 | 1.00 | 1.00 | 32 | 0 | 43 | 30 | 13 |
| | 1:2 | 0.25 | 0.50 | 32 | 0 | 29 | 32 | −3 |
| | 1:2 | 0.50 | 1.00 | 32 | 0 | 43 | 32 | 11 |
| | 2:1 | 0.50 | 0.25 | 46 | 0 | 43 | 46 | −3 |
| | 2:1 | 1.00 | 0.50 | 46 | 0 | 64 | 46 | 18 |
| Emamectin benzoate | 1:1 | 0.25 | 0.25 | 28 | 97 | 100 | 98 | 2 |
| | 1:1 | 0.50 | 0.50 | 28 | 96 | 99 | 97 | 2 |
| | 2:1 | 0.25 | 0.13 | 32 | 97 | 100 | 98 | 2 |
| | 2:1 | 0.50 | 0.25 | 32 | 96 | 100 | 97 | 3 |
| | 2:1 | 1.00 | 0.50 | 32 | 99 | 100 | 99 | 1 |
| | 4:1 | 0.50 | 0.13 | 46 | 96 | 100 | 98 | 2 |
| | 4:1 | 1.00 | 0.25 | 46 | 99 | 100 | 99 | 1 |
| Spinosad | 2:1 | 0.25 | 0.13 | 28 | 33 | 67 | 52 | 14 |
| | 2:1 | 0.50 | 0.25 | 32 | 42 | 89 | 60 | 29 |
| | 4:1 | 0.25 | 0.06 | 28 | 44 | 79 | 60 | 19 |
| | 4:1 | 0.50 | 0.13 | 32 | 33 | 65 | 55 | 11 |

TABLE I-continued

Results for test using *Heliothis virescens*

| Mixture partner | Ratio (gamma:ai's) | Rates applied (ppm) | | Observed % mortality | | | Expected % mortality with mixture | Observed- expected |
|---|---|---|---|---|---|---|---|---|
| | | Gamma | Other ai | Gamma | Other ai | Mixture | | |
| | 4:1 | 1.00 | 0.25 | 46 | 42 | 93 | 68 | 25 |
| | 8:1 | 0.50 | 0.0625 | 32 | 44 | 72 | 62 | 10 |
| | 8:1 | 1.00 | 0.13 | 46 | 33 | 65 | 64 | 1 |
| Chlorpyrifos | 1:05 | 0.50 | 2.50 | 28 | 36 | 42 | 54 | −13 |
| | 1:05 | 1.00 | 5.00 | 28 | 29 | 49 | 49 | −1 |
| | 1:10 | 0.25 | 2.50 | 32 | 36 | 29 | 57 | −27 |
| | 1:10 | 0.50 | 5.00 | 32 | 29 | 49 | 52 | −3 |
| | 1:10 | 1.00 | 10.00 | 32 | 44 | 71 | 62 | 9 |
| | 1:20 | 0.25 | 5.00 | 46 | 29 | 56 | 62 | −6 |
| | 1:20 | 0.50 | 10.00 | 46 | 44 | 63 | 70 | −7 |
| Indoxacarb | 1.25:1 | 0.25 | 0.20 | 28 | 26 | 40 | 47 | −7 |
| | 1.25:1 | 0.50 | 0.40 | 28 | 22 | 40 | 44 | −4 |
| | 1.25:1 | 1.00 | 0.80 | 32 | 26 | 40 | 50 | −10 |
| | 1:1.6 | 0.25 | 0.40 | 32 | 22 | 44 | 47 | −3 |
| | 1:1.6 | 0.50 | 0.80 | 32 | 46 | 60 | 63 | −3 |
| | 2.5:1 | 0.50 | 0.20 | 46 | 22 | 46 | 58 | −12 |
| | 2.5:1 | 1.00 | 0.40 | 46 | 46 | 71 | 71 | 0 |
| Lambda-cyhalothrin | 1:1 | 0.25 | 0.25 | 28 | 46 | 43 | 61 | −18 |
| | 1:1 | 0.50 | 0.50 | 28 | 50 | 41 | 64 | −23 |
| | 1:1 | 1.00 | 1.00 | 32 | 46 | 35 | 63 | −28 |
| | 1:2 | 0.25 | 0.50 | 32 | 50 | 39 | 66 | −27 |
| | 1:2 | 0.50 | 1.00 | 32 | 52 | 38 | 67 | −30 |
| | 2:1 | 0.50 | 0.25 | 46 | 50 | 32 | 73 | −41 |
| | 2:1 | 1.00 | 0.50 | 46 | 52 | 46 | 74 | −28 |

TABLE II

Results for test using *Spodoptera littoralis*

| Mixture partner | Ratio (gamma:ai's) | Rates applied (ppm) | | Observed % mortality | | | Expected % mortality with mixture | Observed- expected |
|---|---|---|---|---|---|---|---|---|
| | | Gamma | Other ai | Gamma | Other ai | Mixture | | |
| Emamectin benzoate | 10:1 | 0.025 | 0.0025 | 0 | 0 | 22 | 0 | 22 |
| | 10:1 | 0.05 | 0.005 | 25 | 6 | 51 | 29 | 22 |
| | 10:1 | 0.1 | 0.01 | 90 | 0 | 82 | 90 | −8 |
| | 20:1 | 0.05 | 0.0025 | 25 | 0 | 32 | 25 | 7 |
| | 20:1 | 0.1 | 0.005 | 90 | 6 | 66 | 90 | −24 |
| | 5:1 | 0.025 | 0.005 | 0 | 6 | 46 | 6 | 40 |
| | 5:1 | 0.05 | 0.01 | 25 | 0 | 76 | 25 | 51 |
| Spinosad | 1:10 | 0.025 | 0.25 | 0 | 0 | 79 | 0 | 79 |
| | 1:10 | 0.05 | 0.5 | 25 | 29 | 96 | 47 | 49 |
| | 1:2.5 | 0.05 | 0.125 | 25 | 0 | 59 | 25 | 34 |
| | 1:2.5 | 0.1 | 0.25 | 90 | 0 | 99 | 90 | 9 |
| | 1:5 | 0.025 | 0.125 | 0 | 0 | 34 | 0 | 34 |
| | 1:5 | 0.05 | 0.25 | 25 | 0 | 82 | 25 | 57 |
| | 1:5 | 0.1 | 0.5 | 90 | 29 | 100 | 93 | 7 |

TABLE III

Results for test using (*Myzus persicae*)

| Mixture partner | Ratio (gamma:ai's) | Rates applied (ppm) | | Observed % mortality | | | Expected % mortality with mixture | Observed- expected |
|---|---|---|---|---|---|---|---|---|
| | | Gamma | Other ai | Gamma | Other | Mixture | | |
| Thiamethoxam | 1:10 | 0.25 | 2.5 | 70 | 92 | 100 | 97 | 3 |
| | 1:10 | 0.5 | 5 | 69 | 94 | 100 | 98 | 2 |
| | 1:2.5 | 0.5 | 1.25 | 69 | 70 | 100 | 91 | 9 |
| | 1:2.5 | 1.0 | 2.5 | 98 | 92 | 100 | 100 | 0 |
| | 1:5 | 0.25 | 1.25 | 70 | 70 | 100 | 91 | 9 |
| | 1:5 | 0.5 | 2.5 | 69 | 92 | 100 | 97 | 3 |
| | 1:5 | 1.0 | 5 | 98 | 94 | 100 | 100 | 0 |

TABLE III-continued

| Results for test using (*Myzus persicae*) | | | | | | | | |
|---|---|---|---|---|---|---|---|---|
| | | Rates applied (ppm) | | Observed % mortality | | | Expected % mortality with | Observed- |
| Mixture partner | Ratio (gamma:ai's) | Gamma | Other ai | Gamma | Other | Mixture | mixture | expected |
| Lambda-cyhalothrin | 1:1 | 0.25 | 0.25 | 70 | 4 | 92 | 71 | 21 |
| | 1:1 | 0.5 | 0.5 | 69 | 14 | 96 | 73 | 23 |
| | 1:2 | 0.25 | 0.125 | 70 | 10 | 66 | 73 | −7 |
| | 1:2 | 1.0 | 0.5 | 98 | 14 | 100 | 98 | 2 |
| | 2:1 | 0.5 | 0.25 | 69 | 4 | 100 | 70 | 30 |
| | 4:1 | 0.5 | 0.125 | 69 | 10 | 98 | 72 | 26 |
| | 4:1 | 1.0 | 0.25 | 98 | 4 | 100 | 98 | 2 |

The invention claimed is:

1. A mixture comprising gamma-cyhalothrin and thiamethoxam, wherein the ratio of gamma-cyhalothrin to thiamethoxam is in the range of 1:2.5 to 1:100 (weight/weight), wherein when the mixture is applied by spraying at a rate of 0.25 ppm gamma-cyhalothrin and 1.25 ppm thiamethoxam onto *Myzus persicae*, the mixture is synergistically effective as determined by the Colby equation, wherein a mortality assessment is made 3 days after application with storage at 20° C.

2. The mixture according to claim 1 further comprising one or more of spinosad, chlorpyrifos, profenofos, lufenuron, indoxacarb and lambda-cyhalothrin.

3. The mixture of claim 1, wherein the ratio of gamma-cyhalothrin to thiamethoxam is in the range of 1:2.5 to 1:10 (weight/weight).

4. The mixture of claim 1, wherein the ratio of gamma-cyhalothrin to thiamethoxam is in the range of 1:10 to 1:100 (weight/weight).

* * * * *